United States Patent [19]

Lemonnier

[11] Patent Number: 5,851,390
[45] Date of Patent: Dec. 22, 1998

[54] ELLIPTICAL FILTRATION UNIT

[75] Inventor: Jean Lemonnier, Paris, France

[73] Assignee: Millipore S.A., Saint-Quentin-En-Yvelines, Cedex, France

[21] Appl. No.: 764,680

[22] Filed: Dec. 11, 1996

[30] Foreign Application Priority Data

May 24, 1996 [FR] France .................................. 96 06505

[51] Int. Cl.⁶ .................................................. B01D 69/10
[52] U.S. Cl. ................................. 210/321.1; 210/321.75; 210/321.84; 210/445
[58] Field of Search ........................... 210/321.1, 321.75, 210/321.84, 433.1, 445, 446, 447, 483, 497.01

[56] References Cited

U.S. PATENT DOCUMENTS

| | | | |
|---|---|---|---|
| 3,520,416 | 7/1970 | Keedwell | 210/490 |
| 4,666,603 | 5/1987 | Madsen et al. | 210/321.1 |
| 4,902,415 | 2/1990 | Lemonnier | 210/321.84 |
| 4,933,084 | 6/1990 | Bandel et al. | 210/500.23 |
| 4,935,142 | 6/1990 | Sternberg | 210/634 |
| 5,112,488 | 5/1992 | Lemonnier | 210/541 |
| 5,141,639 | 8/1992 | Kraus et al. | 210/321.75 |
| 5,269,917 | 12/1993 | Stankowski | 210/232 |
| 5,443,723 | 8/1995 | Stankowski et al. | 210/321.75 |

FOREIGN PATENT DOCUMENTS

| | | |
|---|---|---|
| 0 566 414 A1 | 10/1993 | European Pat. Off. . |
| 71.09576 | 3/1971 | France . |
| 85 13750 | 9/1985 | France . |

*Primary Examiner*—W. L. Walker
*Attorney, Agent, or Firm*—John Dana Hubbard; Timothy J. King; Paul J. Cook

[57] ABSTRACT

A filtration unit containing a filtering membrane, a cover upstream of the membrane, and a base downstream of the membrane, and joined together, characterized in that the filtering membrane has an elliptical shape. This elliptical shape facilitates the use for filtration and allows the unit to be reused without the formation of an air lock when the filtering membrane is partially hydrophobic.

4 Claims, 7 Drawing Sheets

ELLIPTICAL FILTRATION UNIT

BACKGROUND OF THE INVENTION

1.0 Field of the Invention

The present invention relates to a filtration unit, containing a filtering membrane, a part upstream from the membrane forming the cover and a part downstream from the membrane forming the base.

2.0 Description of Prior Art

The three elements of a filtration unit; namely, a membrane, a cover and a base, generally are made of plastic material, and are firmly attached by welding, so as to form the filtration unit, in which the liquid is filtered without any risk of leaking due to the imperviousness of the unit.

The cover often includes a female Luer connector intended to connect the filtration unit to the end of a syringe. The base, situated downstream from the membrane, usually includes a male Luer connector intended to optionally receive a standard hypodermic needle.

In these filtration units, the filtering membrane is welded at its edge, generally of a circular shape or more occasionally of polygonal shape, onto the cover or the base, so as to ensure that the liquid to be filtered passes properly through the filtering membrane, without risk of leaking beyond the periphery of the membrane.

Such filtration units are commonly used in medicine to filter pharmaceutical solutions.

In the filtration units which are marketed in this form, the filtering membrane, which is generally hydrophilic, is supported upstream in the cover and downstream in the base by ribs forming drainage channels which facilitate and direct the flow from the central inlet opening to the totality of the upper surface of the filtering membrane upstream from the latter and the edges of the lower surface of the filtering membrane downstream towards a central outlet opening of the unit.

This double support, both upstream and downstream of the membrane, which is thus sandwiched, avoids any risk of the membrane deteriorating, in the event of back pressure.

However, these filtration units have a certain number of drawbacks.

Their circular shape only allows for fixing of the unit onto the end of a syringe by force in an axial direction and does not permit good visibility of the filtration, despite the use of transparent thermoplastic material for their construction.

The manufacture of a filtering membrane in a circular of hexagonal shape involves a not inconsiderable waste of fairly expensive filtering material.

In addition, the necessity of supporting the filtering membrane both upstream as well as downstream using a set of ribs defining the drainage channels significantly reduces the effective surface area of filtration of the membrane.

An object of the present invention is to overcome disadvantages of the prior art.

This object is achieved by providing the filtering membrane with an elliptical shape and by providing the parts which are upstream serving as a cover and downstream serving as a base, reception and support surfaces for the membrane, in a correspondingly elliptical shape.

As used herein, the terms "ellipse" or "elliptical" means, within the scope of the present invention, an oval shape having a major axis and a minor axis which is in a direction perpendicular to the major axis.

In fact, the Applicant has observed that the elliptical shape of the surface area of the filtering membrane which is obtained by cutting from a continuous roll of fairly expensive filtering material, allows wastage or losses to be reduced by about 4% relative to cutting circular filtering membranes of the same surface area.

Furthermore, the adoption of an elliptical shape for the filtering membrane as well as for the reception and support surfaces of this membrane by the cover and base of the filtration unit allows improved prehension and ergonomics for the user of the filtration unit according to the invention.

In fact, this elliptical shape facilitates the clamping of the unit onto the end of a syringe or reception of a hypodermic needle, similar to a wing nut: the filtration unit of the invention is easier to handle than a unit with a circular shape as it does not twist in the fingers but, on the contrary, allows for a blocking action.

In addition, for the same surface area of filtration as a unit of circular section, the filtration unit having an elliptical section, according to the invention, affords better visibility of the filtrate outlet on the side of the male Luer connector. This, in turn, allows easy verification by slightly inclining the syringe equipped with such a unit in the vertical plane which includes the minor axis of the ellipse.

Moreover, the elliptical shape of a filtration unit has a major axis the length of which is greater than that of the diameter of a filtration unit provided with a circular membrane of the same filtration surface area. This allows the unit, according to the invention, to rest, for example, on the neck of a standard plasma bottle.

Applicant has also discovered that the elliptical filtering membrane of the filtration unit, according to the invention, and which is generally made of hydrophilic material, can contain two hydrophobic areas, positioned at the end portion of the major axis of the ellipse.

Such a structure can be easily manufactured on an industrial scale by cutting ellipses from a continuous roll of hydrophilic filtering material, the outer edges of which have been rendered hydrophobic, or from a continuous roll of hydrophobic filtering material the central part of which is rendered hydrophilic.

A filtration unit of elliptical section, thus provided with a hydrophilic filtering membrane, of which the end portion of the major axis of the ellipse are hydrophobic has quite remarkable properties.

In fact, during successive filtrations with such a unit, the air which is possibly present upstream from the membrane of the filtration unit and/or in the hypodermic syringe with which the filtration unit is fitted, is pushed by the liquid to be filtered towards the edges of the membrane furthest away from the inlet opening and so towards the hydrophobic ends of the major axis of the elliptical filtering membrane and is thus evacuated from the unit without forming a bubble of air, known as an air lock.

Such an effect could be obtained with circular filtering membranes, for example, by a hydrophobic circular peripheral edge. However, such a hydrophobic circular edge would significantly reduce the filtration surface area and would also reduce the filtration yield. In addition, a hydrophobic circular edge is very difficult and expensive to manufacture. Another possibility would consist of providing two diametrically-opposed hydrophobic areas on the circular filtering membrane but, according to this hypothesis, the role of evacuating the air is not at all controlled and depends, in particular, on inclining the membrane in a favoured position.

This control problem is not the case with an elliptical filtering membrane all the central part of which, up to and including the ends of the minor axis of the ellipse are hydrophilic and only the end parts corresponding to the ends of the major axis of the ellipse are hydrophobic. In this structure, the trapped air and the liquid to be filtered move from the central inlet part towards the outside so as to spread circumferentially over a distance corresponding to the minor axis of the ellipse. Having arrived at the ends of the minor axes of the ellipse, it flows back towards the parts furthest away which correspond to the end portions of the major axis of the ellipse, where the presence of small hydrophobic areas or hydrophobic spots allows the trapped air to be evacuated, thereby, preventing the formation of an air lock.

A consequence of the present invention is that, not only is the phenomenon of air locks which were disabling conventional filtrations using circular filtration units eliminated for the first time, without a significant reduction in the filtering surface area of the filtration unit, but also filtration units are now available which are reusable for performing several successive filtrations.

Naturally, it is advisable to rationally use the maximum filtering surface area for the filtration of the liquid to be filtered by optimizing the proportion of hydrophilic filtering area of the membrane to the detriment of the proportion of hydrophobic filtering area. This requirement is easily satisfied by having only two small hydrophobic areas or two hydrophobic spots positioned at the end portions of the major axis of each elliptical filtering membrane and corresponding to two hydrophobic trips or two series of hydrophobic spots arranged on the edges of a continuous roll of hydrophilic filtering material, from which the elliptical filtering membranes are formed according to the invention.

An additional advantage of the filtration unit of this invention is the appreciable reduction in the dead volume in which the filtered liquid is retained.

In fact, in conventional circular filtration units, the filtered liquid, which can be a particularly expensive product, is retained not only by porosity in the constitutive channels of the hydrophilic filtering material itself but also in all the dead volume positioned beneath the filtering membrane, where it can be easily seen when the liquid in question is coloured. This occurs despite a network of ribs supporting the membrane and evacuation channels directing all of the filtered liquid collected at the lower part of the filtering membrane from its ends towards a central evacuation opening.

By contrast, in the filtration units with an elliptical section, according to the invention, the filtered liquid of course remains retained by porosity in the constitutive channels of the hydrophilic filtering material itself but there is no longer any dead volume positioned beneath the filtering membrane and where the filtered liquid can be retained. In fact, the hydrophobic areas positioned at the ends of the major axis of the elliptical filtering membrane allow air to pass, which drives any trace of liquid present away from said hydrophobic ends to the central evacuation portion.

Such a phenomenon is easily detectable by an examination of the disappearance of colouration in the base positioned downstream from the filtration unit, when the filtered liquid is coloured.

As a consequence, the elliptical surface of the support and reception area for the filtering membrane in the base, positioned downstream from the membrane, can contain, as well as an elliptical peripheral edge receiving the ends of the membrane, a multitude of rounded points, the tops of which are flush with the same level as said elliptical peripheral edge. It is therefore no longer necessary to provide in this support part, positioned downstream from the membrane, any guide channels for the flow of liquid or for the evacuation of air from the edges of the filtering membrane surface to the central outlet opening, as was the case for the filtration units with prior membrane having circular surface area.

Moreover, it will be noted that such a support for the filtering membrane, downstream, by rounded points, has an additional double advantage. One advantage compares reducing the contact area between the filtering membrane and the support and of increasing the performance of a given area of filtering membrane. In addition, the filtration can be performed under pressure without the risk of rupturing the membrane.

BRIEF DESCRIPTION OF THE DRAWINGS

The present invention will now be described with the help of the attached drawings in which.

DESCRIPTION OF SPECIFIC EMBODIMENTS

The filtration unit represented in FIGS. 1A to D, 2A to C, 3A to B and 4A represent a first preferred use of the present invention.

It is represented with all its assembled elements in FIGS. 1A to D, namely an upstream part forming the cover 2, a downstream part forming the base 3 and a filtering membrane 4, which are welded such as by using ultrasonics, in order to form the filtration unit 1. The filtration unit is presented in the form of a top having an oval or elliptical cross-section, the axis of which corresponds to that of the inlet and outlet openings for the liquid to be filtered.

Figure 2A:
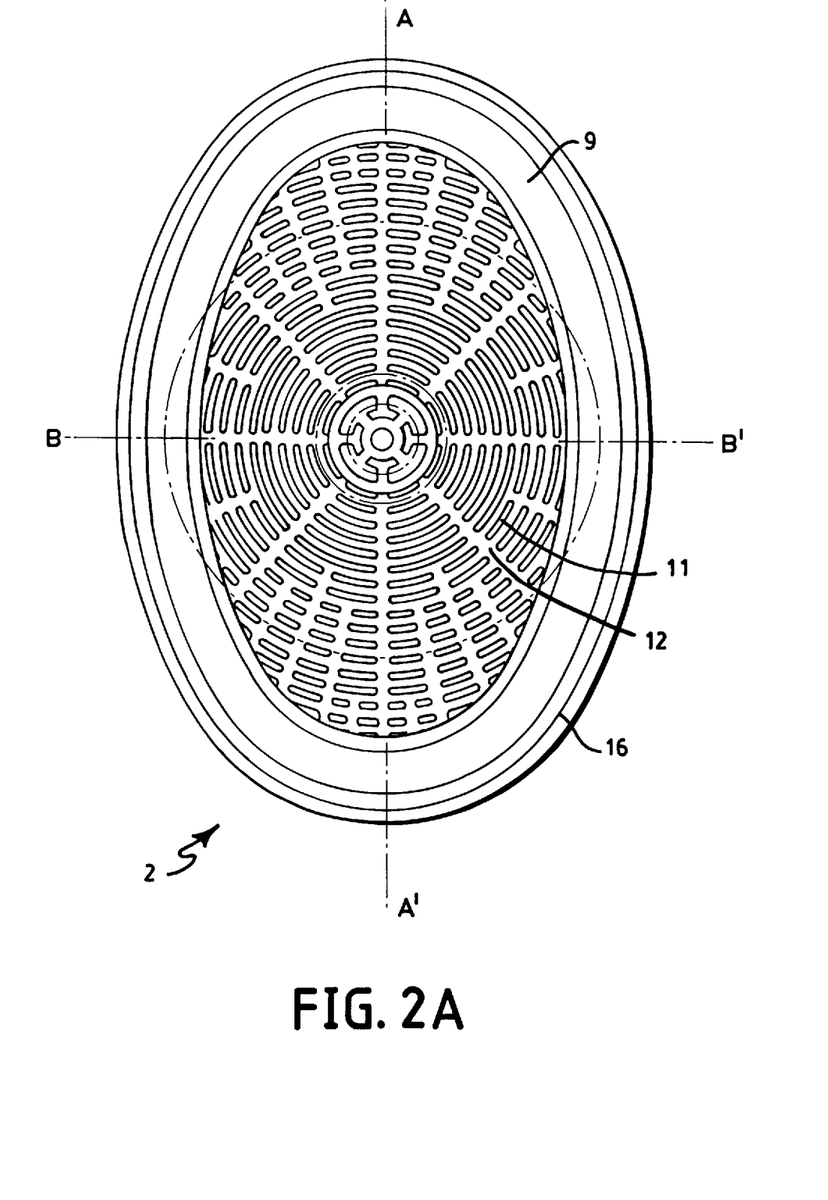
FIGS. 2A, 2B and 2C represent respectively a bottom view (2A), a section along axis AA' (2B) and a section along axis BB' (2C) upstream from the filtering membrane, of a filtration unit according to the invention.
Figure 2B:
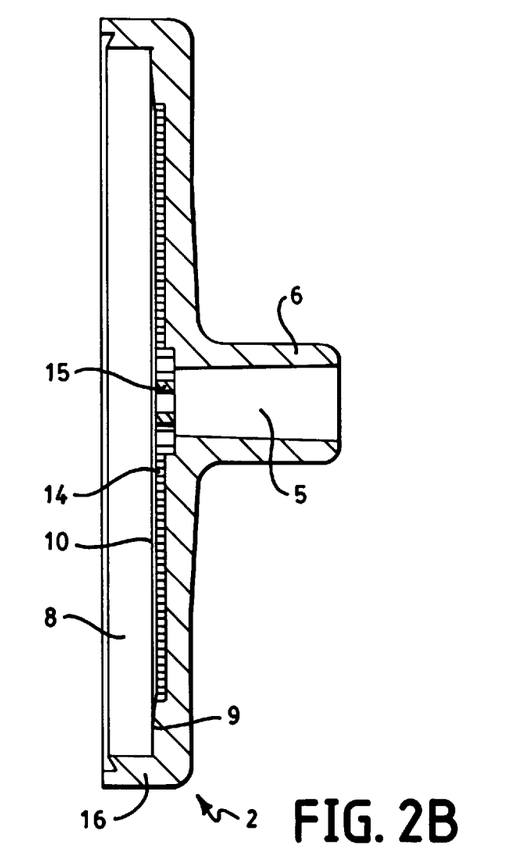
Figure 2C:
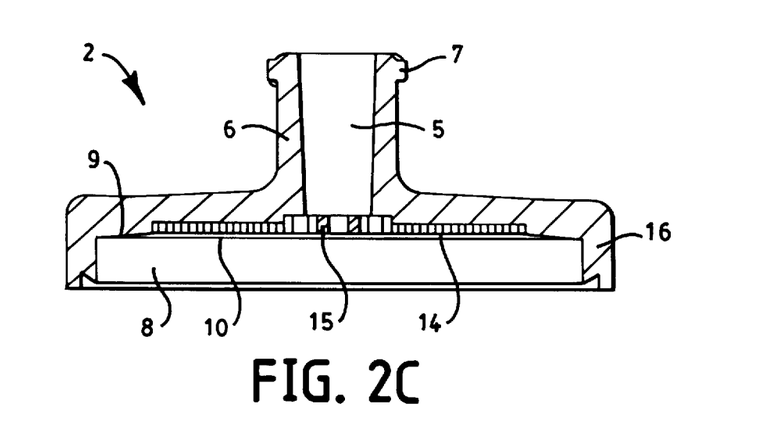

The upstream part forming the cover 2 is illustrated in FIGS. 2A, 2B and 2C. It is composed of an elliptical cover 2 including a central inlet opening 5, opening towards the top in the form of a standard female Luer connector 6, provided at its upper end with an external threaded cap 7. The cover 2 has an elliptical cross-section, the edge portions, 16 of which are orientated downwards (see FIG. 2C) so as to define a space 8, the bottom of which is provided with a plan elliptical outer ring 9. A central part 10 is formed by circular ribs 11 separated by radial 12. Circular 13 channels and the tops 14 of which are situated in the same plane as the plane outer ring 9. The opening of the Luer connector 6 into the bottom of the cover is also provided with a cross-piece 15 intended to distribute the inlet flow of liquid to be filtered over the entire bottom of the cover 2.

Figure 1A:
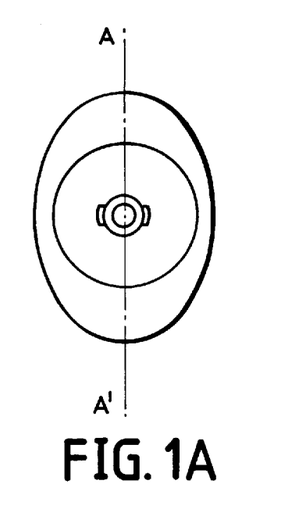
FIGS. 1A, 1B, 1C and 1D represent a first use of a filtration unit according to the invention according to, respectively, a topview (1A), a view from the left-hand side (1B), a view from the right-hand side (1C), and an axial cross-section view along axis AA' of FIG. 1A seen from the right-hand side (1D)
Figure 1B:
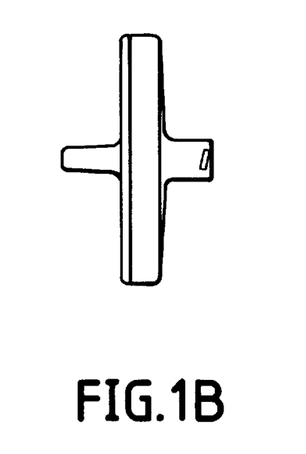
Figure 1C:
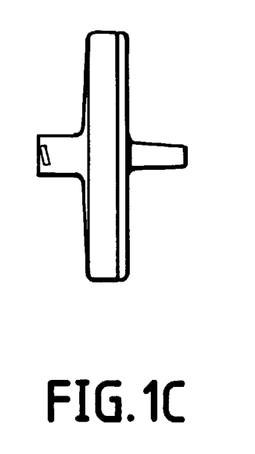
Figure 1D:
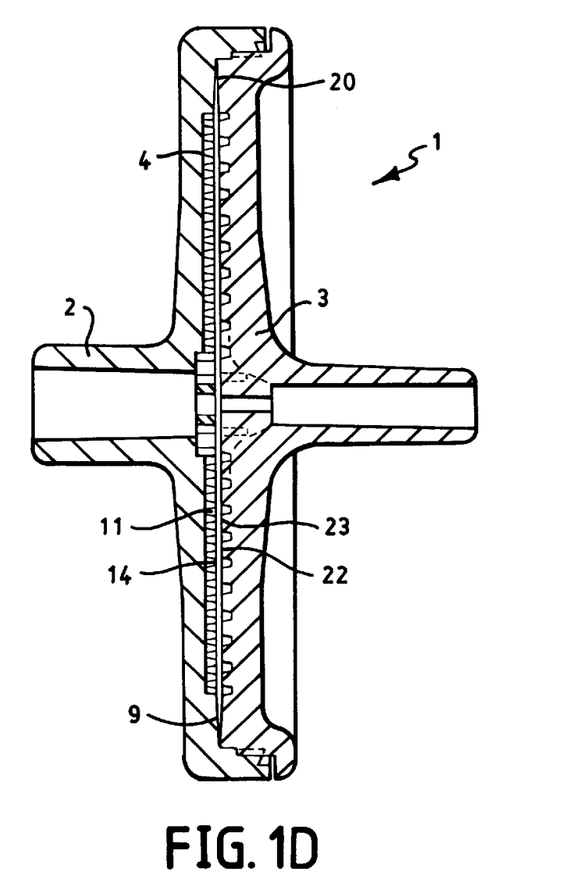

As is shown in more detail in FIG. 1D, the bottom of the cover is constituted by the plane outer ring 9 and the tops 14 of the ribs 11 situated in the same plane, perpendicular to the axis of the filtration unit. The bottom of the cover has an elliptical shape appropriate for receiving a filtration membrane 4 having a corresponding elliptical shape, the periphery of which will rest on the plane outer ring 9 and the central part of which will be supported, for example, by all of tops of the ribs 11.

Figure 3A:
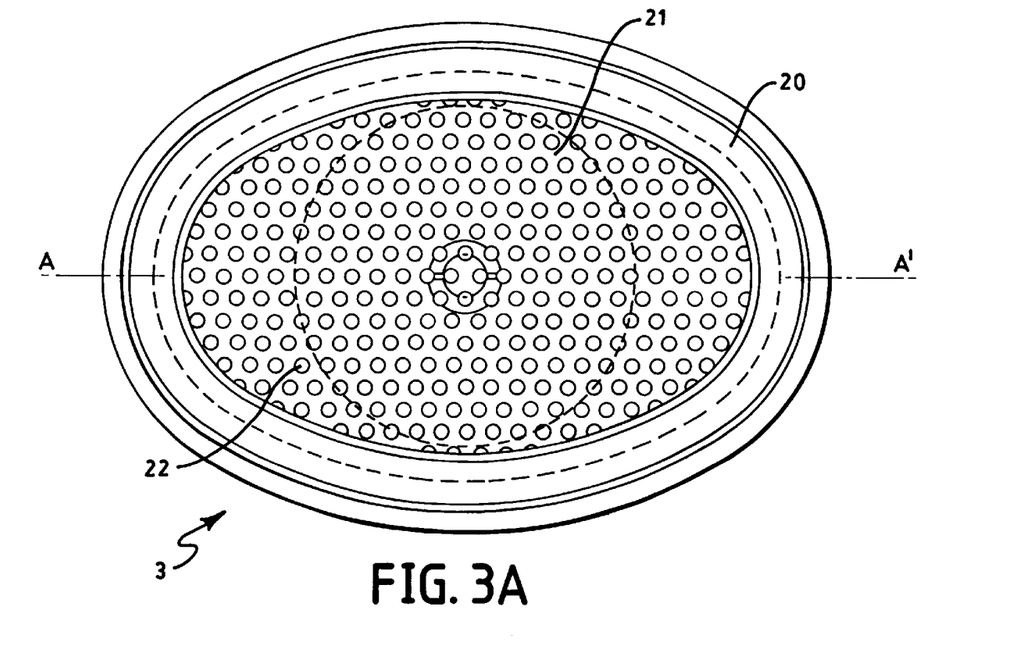
FIGS. 3A and 3B represent respectively a topview (3A) and a section along axis AA' of FIG. 3A of the base part (3B), situated downstream from the filtering membrane, of a filtration unit according to the invention.
Figure 3B:
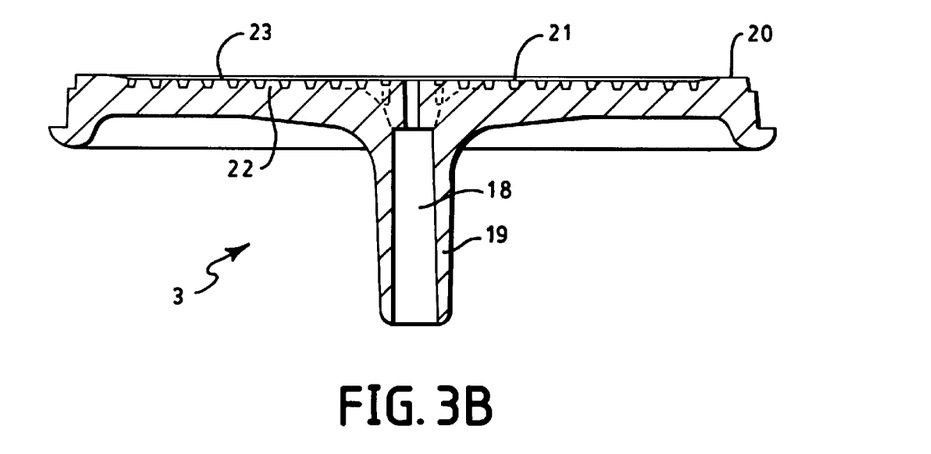

The downstream part forming the base 3 is illustrated in FIGS. 3A and 3B; it is composed of a plate 17 containing a central outlet opening 18 which opens downwards in the form of a standard male Luer connector 19. The plate 17 has an elliptical cross-section, the dimensions of which are determined so as to able to tightly fit inside the space 8 of the cover 2 as shown in FIG. 1D. The plate 17 is provided with a plane elliptical outer ring 20 and a recessed central part 21, the bottom of which contains a multitude of rounded points 22. The tops 23 of the points 22 are positioned in the same plane as the plane outer ring 20 in order to support the filtering membrane 4. The axes of the points 22 are all parallel to that of the filtration unit 1. The opening of the Luer connector 19 onto the plate 17 is also provided with points 22 intended to support the filtering membrane 4.

As is shown in more detail in FIG. 1D, the filtering membrane 4 is sandwiched between the tops 23 of the points of plate 17 of the base 3 and the tops 14 of the ribs 11 of the cover 2. Its peripheral edges are also sandwiched between the plane elliptical outer rings 20 of the base 3 and 9 of the cover 2.

Figure 4A:
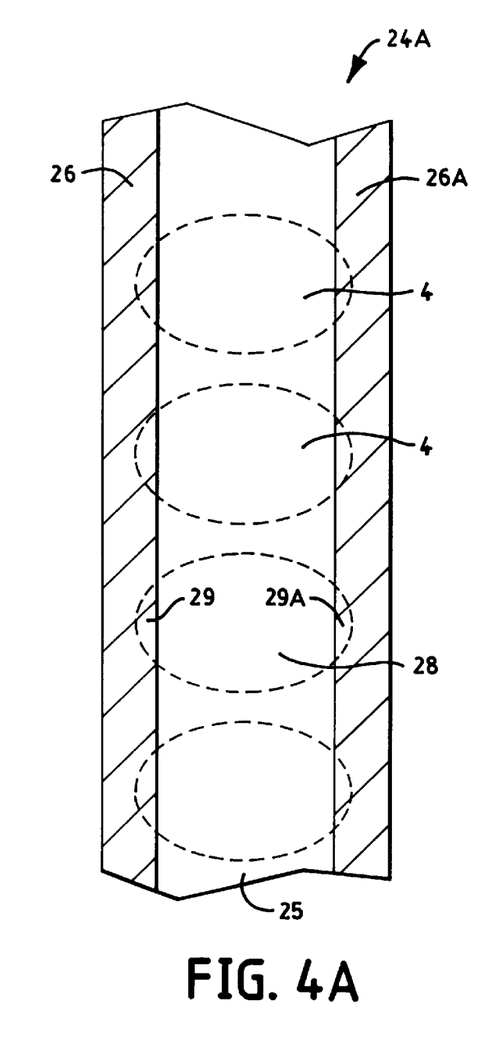
FIGS. 4A and 4B represent a continuous roll of filtering material from which the elliptical filtering membranes for a filtration unit according to the invention are cut, either with two hydrophobic strips at its edges (FIG. 4A) or with a series of hydrophobic spots at its same edges (FIG. 4B)
Figure 4B:
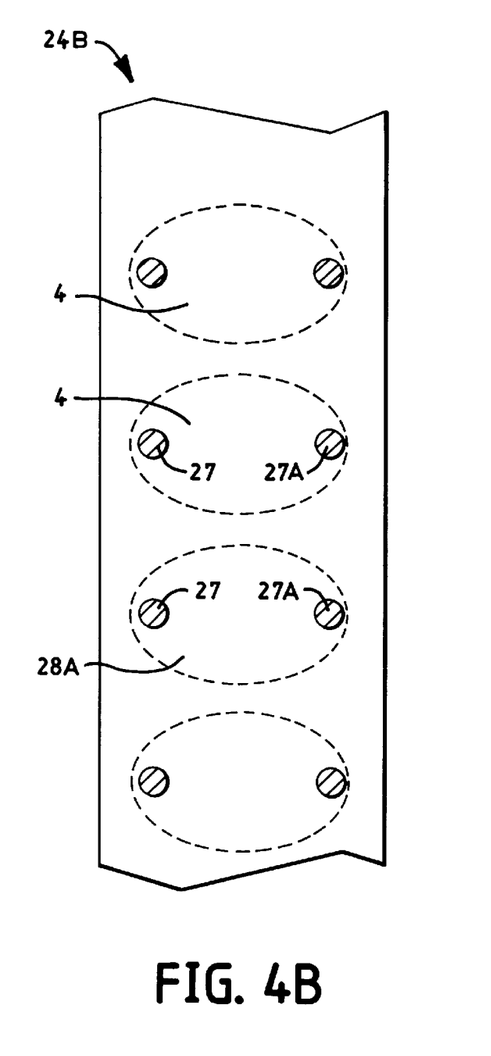

The filtering membrane 4 of elliptical shape, according to the invention, can be formed, for example, by being cut out using a hollow punch from a continuous roll 24A or 24B or filtering material, as shown in FIGS. 4A or 4B respectively.

The long-length continuous roll 24A of filtering material contains a hydrophilic central area 25 and hydrophobic edge strips 26 and 26A on its two lateral edges.

The cutting, using a hollow punch, from this roll 24A of filtering membranes 4 has an elliptical section. The ends of the major axis of the ellipses are positioned in the strips 26 and 26A allow membranes 4 to be obtained wherein the central main part 28 is hydrophilic and only small areas 29 and 29A, positioned at the end portions of the major axis of each ellipse, are hydrophobic.

Similarly, the continuous roll 24B of hydrophilic filtering material, represented in FIG. 4B, can be provided, on each of its continuous edges, with a series of hydrophobic spots 27 or 27A, intended, after cutting out with a hollow punch of ellipses from the roll 24B, to be found at the end portions of the major axis of each elliptical filtering membrane 4. Such cutting out of elliptical filtering membranes 4 can be easily carried out using automatic machinery and allows a saving of approximately 4% of the surface area of the roll of filtering material as compared to the manufacture of circular filtering membranes with the same surface area.

Figure 5A:
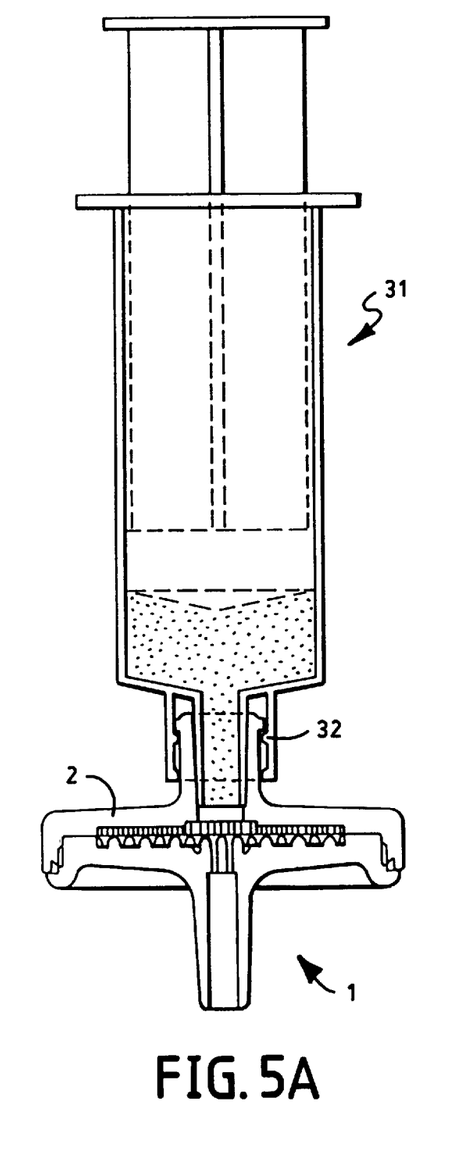
FIGS. 5A and 5B represent a syringe and a filtration unit according to the preceding figures respectively connected (5A) or not connected (5B) with a screwable male Luer connector provided on the syringe and FIG. 6 represents a syringe and a filtration unit according to the invention in another use according to the invention.
Figure 5B:
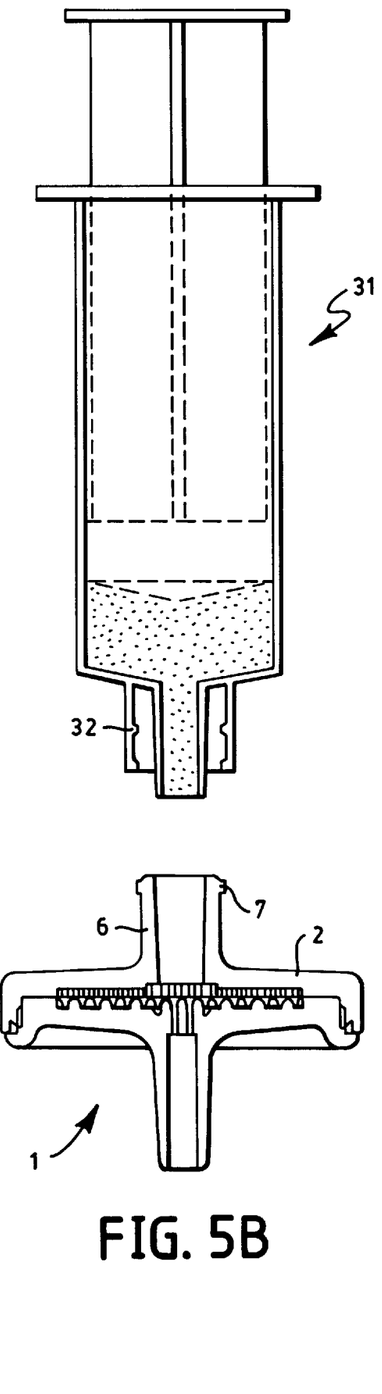

FIGS. 5A and 5B illustrate the cooperation of an elliptical filtration unit 1 according to the invention with a hypodermic syringe 31.

As these figures show schematically, the male Luer connector of the syringe 31 is surrounded by an external skirt 32 which is threaded internally and which can cooperate with the external threaded cap 7 of the female Luer connector 6 of the cover 2.

Figure 6:
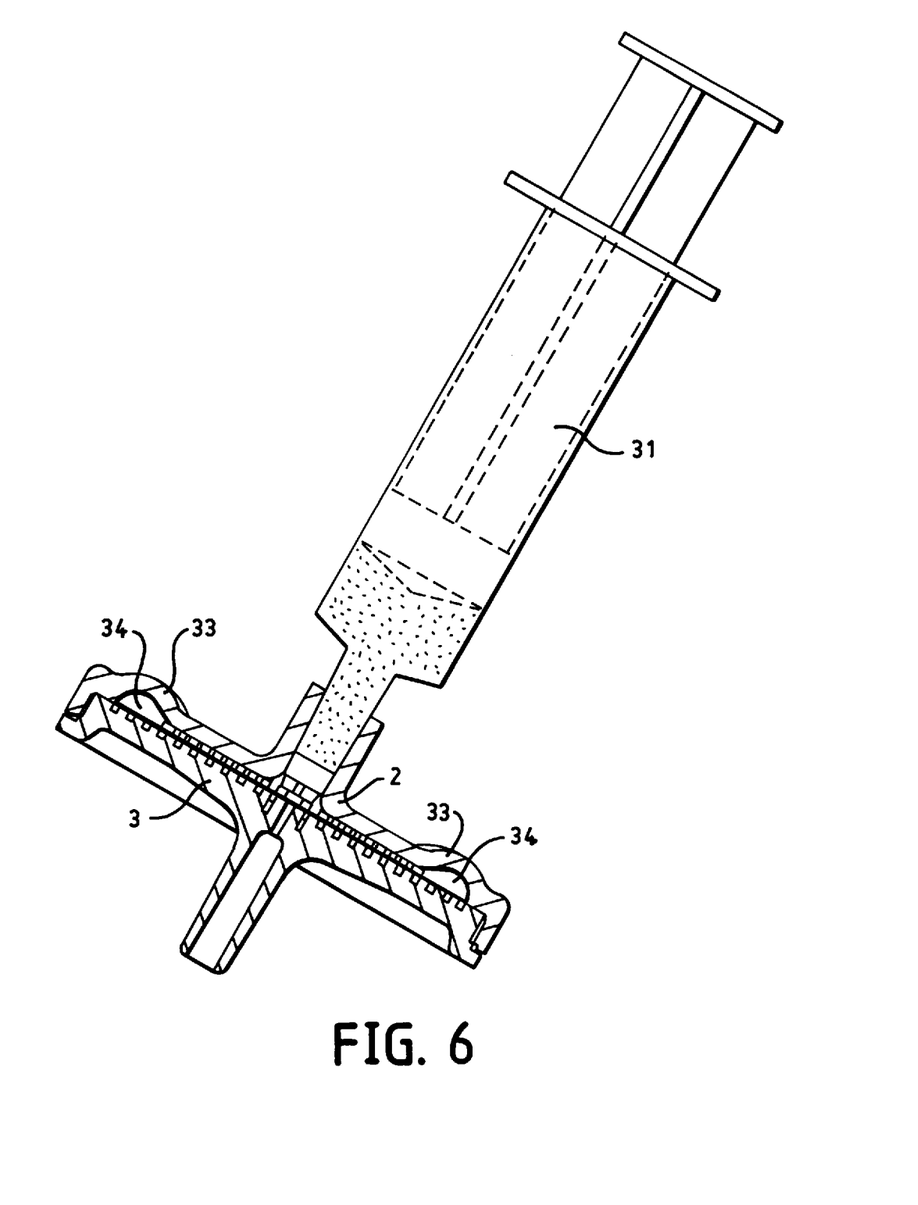

FIG. 6 illustrates the cooperation of another use of the invention with a hypodermic syringe 31.

In this other use, the filtration unit 1 essentially differs from that illustrated in the preceding Figures by the fact that the elliptical cover 2 contains blisters 33 of concave half-bean shape at the end portions of the major axis of the ellipse and by the fact that the filtering membrane 4 with which it is fitted is entirely hydrophilic.

These blisters 33 serve as air traps and are intended to store the air bubbles present in the cover 2, upstream from the filtering membrane 4 and to stop air lock, i.e., the air trapped in the filtration unit from obstructing access to the upper surface area of the totally hydrophilic filtering membrane by the liquid to be filtered. During successive filtrations with such a unit, according to FIG. 6, these traps 34 prevent, in the case of air being introduced upstream from the filtering membrane 4, the air spreading into the area of the drainage channels 12 and 13 and therefore significantly reducing the filtration area of the membrane. These traps 34 remedy this risk and allow the central filtration surface of the unit to remain free.

The base materials used for the manufacture of filtration units according to the invention are known from the prior art. Essentially, they are thermoplastic materials, preferably transparent, for the cover and the base of the filtration unit, such as polystyrene, polyolefins such as polyethylene, polypropylene or ethylene-propylene copolymers, polyesters and polyvinyl chloride.

The base material for the filtering membrane 4 is a plastic material which is known per se and may consist in particular of a sheet of polyester sulphone or cellulose ester having a large number of pores.

The different elements of the filtration unit according to the invention are assembled by ultra-sound welding and the unit obtained can have different dimensions corresponding to the different uses for which it is intended.

The elliptical shape of these different elements is characterized by a major axis and a minor axis, the respective proportions of which are illustrated in the attached drawings.

Thus the length of the minor axis of the ellipse can represent between 50 and 75% of the length of the major axis and preferably ⅔ of the length of the latter.

I claim:

1. A filtration unit which comprises:

a filtration membrane having pores which permit filtration of a fluid through said membrane, said membrane being free of holes other than said pores, and having a shape of a solid ellipse, said membrane being hydrophilic and having a small hydrophobic area positioned at each end portion of the major axis of the ellipse, a cover having a fluid inlet said cover having a shape of an ellipse, a base having a fluid outlet, said base having a shape of an ellipse, said cover and said base being joined together with said filtration membrane positioned between said cover and said base to form a seat about the entire periphery of said membrane.

2. The filtration unit according to claim 1 characterized in that elliptical surfaces for receiving and supporting for the filtering membrane in the cover, include support ribs defining channels which guide flow of liquid or evacuation of air from a central inlet opening over the elliptical area of the filtering membrane.

3. The filtration unit according to claim 1 characterized in that elliptical surface area for receiving and supporting the filtering membrane in the base includes a multitude of rounded points free of guide channel for flow of liquid or evacuation of air from end portions of the elliptical area of the filtering membrane to a central outlet opening.

4. The filtration unit according to any one of claims 1, 2 or 3, characterized in that the cover has a plurality of concave blisters, in which form traps and which are positioned at end portions of the major axis of the ellipse.

* * * * *